(12) United States Patent
Lemprecht et al.

(10) Patent No.: US 9,765,116 B2
(45) Date of Patent: Sep. 19, 2017

(54) INHIBITORS OF THE EPH-A RECEPTOR AND USES THEREOF

(71) Applicant: Carmel Haifa University Economic Corporation Ltd., Haifa (IL)

(72) Inventors: Raphael Lemprecht, Haifa (IL); Monica Dines, Haifa (IL)

(73) Assignee: CARMEL HAIFA UNIVERSITY ECONOMIC CORPORATION LTD., Haifa (IL)

(*) Notice: Subject to any disclaimer, the term of this patent is extended or adjusted under 35 U.S.C. 154(b) by 0 days.

(21) Appl. No.: 14/785,456

(22) PCT Filed: Apr. 13, 2014

(86) PCT No.: PCT/IL2014/050359
§ 371 (c)(1),
(2) Date: Oct. 19, 2015

(87) PCT Pub. No.: WO2014/170900
PCT Pub. Date: Oct. 23, 2014

(65) Prior Publication Data
US 2016/0083428 A1 Mar. 24, 2016

Related U.S. Application Data

(60) Provisional application No. 61/813,195, filed on Apr. 18, 2013.

(51) Int. Cl.
| | |
|---|---|
| C07K 2/00 | (2006.01) |
| C07K 4/00 | (2006.01) |
| C07K 5/00 | (2006.01) |
| C07K 7/00 | (2006.01) |
| A61K 38/00 | (2006.01) |
| A61K 49/00 | (2006.01) |
| A61B 5/00 | (2006.01) |
| C07K 14/00 | (2006.01) |
| C07K 14/705 | (2006.01) |
| C07K 7/08 | (2006.01) |
| C07K 14/52 | (2006.01) |
| C07K 7/06 | (2006.01) |

(52) U.S. Cl.
CPC .............. C07K 7/08 (2013.01); C07K 7/06 (2013.01); C07K 14/52 (2013.01); A61K 38/00 (2013.01)

(58) Field of Classification Search
CPC .......... C07K 16/2866; A61K 47/48246; A61K 38/00; A61K 38/177; A61K 47/481; A61K 47/48415; A61K 49/0056; A61K 51/088; G01N 33/5058
See application file for complete search history.

(56) References Cited

U.S. PATENT DOCUMENTS

| | | | |
|---|---|---|---|
| 4,666,828 A | 5/1987 | Gusella | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson | |
| 8,461,119 B2* | 6/2013 | Pasquale | A61K 47/48246 514/13.3 |
| 9,320,812 B2* | 4/2016 | Hampl | A61K 47/48246 |
| 2004/0180823 A1* | 9/2004 | Pasquale | A61K 47/48246 514/8.3 |
| 2005/0049194 A1* | 3/2005 | Frisen | C07K 14/715 424/130.1 |
| 2014/0093495 A1* | 4/2014 | Hampl | A61K 47/48246 424/133.1 |
| 2014/0302034 A1* | 10/2014 | Bankovich | A61K 47/48246 424/136.1 |
| 2016/0257745 A1* | 9/2016 | Hampl | C07K 16/28 |

FOREIGN PATENT DOCUMENTS

| | | | | |
|---|---|---|---|---|
| WO | WO2004/028551 | * | 4/2004 | ............. A61K 38/00 |
| WO | 2010141974 | | 12/2010 | |
| WO | WO2012/078813 | * | 6/2012 | ........... A61K 39/395 |
| WO | WO2012/118547 | * | 9/2012 | ........... A61K 39/395 |

OTHER PUBLICATIONS

Boulaflous et al. BM Plant Biol. 2009; 9:144.*
Frobel et al. Nature communications 2012; 3: 1311.*
Burgess et al. J of Cell Bio. 1990, 111:2129-2138.*
Bowie et al. Science, 1990, 247:1306-1310.*
Pawson et al. 2003, Science 300:445-452.*
Chapman-Smith et al. J. Nutri. 1999; 129:477S-484S.*
Sharma et al. PLoS One Jul. 9, 2010, 5: e11496.*
Koolpe et al., "An Ephrin Mimetic Peptide That Selectively Targets the EphA2 Receptor", J. Biol. Chem. 2002, 46974-46979.
Savelieva et al., "Learning and Memory Impairment in Eph receptor A6 knockout mice", Neuroscience Letters 438, 2008 (205-209).
Dines M., Lamprecht R., "EphrinA4 mimetic peptide targeted to EphA binding site impairs the formation of long-term fear memory in lateral amygdala" Transl. Psychiatry, 2014.
Genbank accession No. CAA06993.1, Oct. 2008.
Genbank accession No. CAA06992.1, Oct. 2008.
Genbank accession No. AAI07484.1, Jun. 2006.
Genbank accession No. NP_872631.1, Apr. 2016.
Genbank accession No. NP_005218.1, Apr. 2016.
Genbank accession No. NP_872632.2, Apr. 2106.
Genbank accession No. EAW53140.1, Mar. 2015.
Genbank accession No. EAW53139.1, Mar. 2015.
Genbank accession No. EAW53138.1, Mar. 2015.
Genbank accession No. NP_131936.2, Feb. 2015.
Genbank accession No. EDL15210.1, Mar. 2015.

(Continued)

*Primary Examiner* — Chang-Yu Wang
(74) *Attorney, Agent, or Firm* — The Roy Gross Law Firm, LLC; Roy Gross

(57) ABSTRACT

Eph A receptor inhibitor peptides, and particularly Eph A4 receptor inhibitor peptides, are provided. The peptides comprise a sequence derived from the G-H loop of ephrin A4. Further, pharmaceutical compositions comprising said peptides and use thereof in treating, ameliorating or preventing diseases associated with memory formation are provided.

14 Claims, 7 Drawing Sheets

(56) References Cited

OTHER PUBLICATIONS

Genhank accession No. O08542.2, Feb. 2016.
Genbank accession No. AAI60329.1, Apr. 2008.
Genbank accession No. BAE25127.1, Oct. 2010.
Genbank accession No. BAB28092.1, Oct. 2010.
Genbank accession No. AAB50238.1, Mar. 1997.
Genbank accession No. XP_006976391.1, Mar. 2016.
Genbank accession No. XP_006976390.1, printed May 2016.
Patricia Menzel et al., Ephrin-A6, a New Ligand for EphA Receptors in the Developing Visual System, Developmental Biology, Feb. 2001, pp. 74-88, vol. 230, Issue 1, La Jolla, California.

* cited by examiner

SEQUENCE LISTING

```
<160> NUMBER OF SEQ ID NOS: 11

<210> SEQ ID NO 1
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = Tyr or Phe
<220> FEATURE:
<221> NAME/KEY: MISC_FEATURE
<222> LOCATION: (7)..(7)
<223> OTHER INFORMATION: Xaa = Pro or Ser

<400> SEQUENCE: 1

Gln Arg Xaa Thr Pro Phe Xaa Leu Gly Phe Glu
1               5                   10

<210> SEQ ID NO 2
<211> LENGTH: 11
<212> TYPE: PRT
<213> ORGANISM: Mus musculus

<400> SEQUENCE: 2

Gln Arg Tyr Thr Pro Phe Pro Leu Gly Phe Glu
1               5                   10

<210> SEQ ID NO 3
<211> LENGTH: 11
<212> TYPE: PRT
<213> ORGANISM: Homo sapiens

<400> SEQUENCE: 3

Gln Arg Phe Thr Pro Phe Ser Leu Gly Phe Glu
1               5                   10
```

```
<210> SEQ ID NO 4
<211> LENGTH: 13
<212> TYPE: PRT
<213> ORGANISM: Artificial
<220> FEATURE:
<223> OTHER INFORMATION: Synthetic peptide

<400> SEQUENCE: 4

Arg Arg Gln Arg Tyr Thr Pro Phe Pro Leu Gly Phe Glu
1               5                   10

<210> SEQ ID NO 5
<211> LENGTH: 13
<212> TYPE: PRT
<213> ORGANISM: Artificial
<220> FEATURE:
<223> OTHER INFORMATION: Synthetic peptide

<400> SEQUENCE: 5

Arg Arg Gln Arg Phe Thr Pro Phe Ser Leu Gly Phe Glu
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic peptide

<400> SEQUENCE: 6

Gln Arg Tyr Thr Pro Phe Pro Leu Gly Phe Glu Lys
1               5                   10

<210> SEQ ID NO 7
<211> LENGTH: 12
<212> TYPE: PRT
<213> ORGANISM: Artificial
<220> FEATURE:
<223> OTHER INFORMATION: Synthetic peptide

<400> SEQUENCE: 7

Gln Arg Phe Thr Pro Phe Ser Leu Gly Phe Glu Lys
1               5                   10

<210> SEQ ID NO 8
<211> LENGTH: 14
<212> TYPE: PRT
<213> ORGANISM: Artificial
<220> FEATURE:
<223> OTHER INFORMATION: Synthetic peptide

<400> SEQUENCE: 8

Arg Arg Gln Arg Tyr Thr Pro Phe Pro Leu Gly Phe Glu Lys
1               5                   10

<210> SEQ ID NO 9
<211> LENGTH: 14
<212> TYPE: PRT
<213> ORGANISM: Artificial
<220> FEATURE:
<223> OTHER INFORMATION: Synthetic peptide

<400> SEQUENCE: 9

Arg Arg Gln Arg Phe Thr Pro Phe Ser Leu Gly Phe Glu Lys
1               5                   10

<210> SEQ ID NO 10
```

```
<211> LENGTH: 13
<212> TYPE: PRT
<213> ORGANISM: Artificial
<220> FEATURE:
<223> OTHER INFORMATION: Synthetic peptide

<400> SEQUENCE: 10

Arg Arg Trp Ser Gly Tyr Glu Ala Cys Thr Ala Glu Gly
1               5                   10

<210> SEQ ID NO 11
<211> LENGTH: 13
<212> TYPE: PRT
<213> ORGANISM: Artificial
<220> FEATURE:
<223> OTHER INFORMATION: Synthetic peptide

<400> SEQUENCE: 11

Arg Phe Thr Pro Phe Ser Leu Gly Phe Glu Phe Leu Pro
1               5                   10
```

INHIBITORS OF THE EPH-A RECEPTOR AND USES THEREOF

This application is a U.S. National Phase of International Application No. PCT/IL2014/050359, filed Apr. 13, 2014, which claims priority to U.S. Provisional Application No. 61/813,195, filed Apr. 18, 2013, the disclosures of which are hereby incorporated by reference in their entireties.

FIELD OF THE INVENTION

Embodiments of the invention relate to inhibitors of the EphA receptor and methods of treating disease using the inhibitors.

BACKGROUND OF THE INVENTION

Eph receptors (Ephs) are a group of transmembrane receptors found in human and animal cells from the family of receptor tyrosine kinases. Eph receptors identify intercellular interactions by transmitting signals into cells in which they are located following binding to their corresponding ephrin ligands, transmembranal ligands generally attached to an opposing cell surface.

Ephs may be divided into two general classes: EphA and EphB. Humans express nine EphAs and five EphBs. Generally, Ephs of specific class preferentially bind ephrins of the corresponding class. However, there are exceptions to this, for example, binding of EphA4 by ephrin-B3 and ephrin-B2.

Eph-ephrin interactions mediate many cell-cell interactions in the human body including interactions relating to embryo formation, memory formation, neuron formation and cancer.

There is a need for an inhibitory peptide specific to EphA receptor, particularly EphA4, effective in treating EphA related disease, and particularly in humans, including but not limited to post-traumatic stress disorder (PTSD). The present invention addresses these needs.

SUMMARY OF THE INVENTION

The present invention provides peptides derived from the G-H loop of ephrin A4, and pharmaceutical compositions comprising same effective in treating or ameliorating diseases associated with memory formation.

The inventors have synthesized new peptides comprising a sequence of the G-H loop of ephrin A4. The invention is based, in part, on the finding that the peptides are effective in binding to EphA receptors. In animal models, an exemplary peptide was shown to advantageously bind the EphA4 receptor and inhibit memory formation, thereby indicating that the peptides may be used to treat diseases associated with memory formation in humans, including but not limited to post-traumatic stress disorder (PTSD).

Accordingly, an aspect of embodiments of the invention relates to an isolated peptide comprising an amino acid sequence as set forth in SEQ ID NO: 1 (QRX$_1$TPFX$_2$LGFE), wherein X$_1$ is Tyr (Y) or Phe (F) and X$_2$ is Pro (P) or Ser (S), or a sequence having a conservative substitution relative to SEQ ID NO: 1.

According to one embodiment, the peptide comprises the amino acid sequence as set forth in SEQ ID NO: 2 (QRYTPFPLGFE). According to another embodiment, the peptide comprises the amino acid sequence as set forth in SEQ ID NO: 3 (QRFTPFSLGFE).

According to additional embodiments, the peptide further comprises 1-4 arginine residues contiguous to the peptide's N-terminus. According to some embodiments, the peptide comprises the amino acid sequence as set forth in SEQ ID NO: 4 (RRQRYTPFPLGFE). According to particular embodiments, the peptide consists of the amino acid sequence as set forth in SEQ ID NO: 4 (RRQRYTPFPLGFE). According to another embodiment, the peptide comprises the amino acid sequence as set forth in SEQ ID NO: 5 (RRQRFTPFSLGFE). According to another particular embodiment, the peptide consists of the amino acid sequence as set forth in SEQ ID NO: 5 (RRQRFTPFSLGFE).

According to another embodiment, the peptide further comprises at least one lysine residue contiguous to the peptide's C-terminus. According to another embodiment, the peptide further comprises one lysine residue contiguous to the peptide's C-terminus. According to some embodiments, the peptide comprises the amino acid sequence as set forth in SEQ ID NO: 6 (QRYTPFPLGFEK). According to some embodiments, the peptide comprises the amino acid sequence as set forth SEQ ID NO: 7 (QRFTPFSLGFEK).

Peptides according to embodiments of the invention may comprise amino acid modifications which comprise natural or synthetic amino acids. Peptides according to embodiments of the invention may comprise amino acid modifications such as acetylation including N-terminal acetylation or amidation. According to a particular embodiment, the N-terminus of said peptide is acetylated.

According to some embodiments, said peptide is an inhibitor of an ephrin type-A (EphA) receptor. In a particular embodiment, said EphA receptor is EphA4 receptor.

According to another aspect, there is provided a pharmaceutical composition comprising as an active ingredient an isolated peptide of the present invention, and a pharmaceutically acceptable carrier.

In some embodiments, the pharmaceutical composition is formulated for systemic administration. Systemic administration includes but is not limited to administration modes selected from intravenous administration, subcutaneous administration, inhalation, intradermal administration, transdermal administration, transmucosal administration, and/or oral administration.

According to another aspect, there is provided a method of treating, preventing or alleviating a disease in a subject, particularly a disease associated with EphA4 receptor, the method comprises administering to the subject in need thereof an effective amount of the peptide of the invention or the pharmaceutical composition comprising same.

According to some embodiments, the disease is associated with memory formation. According to another embodiment, the disease is associated with long-term memory formation.

According to another embodiment, said memory formation is a fear-related memory formation. According to some embodiments, the disease is selected from the group consisting of post-traumatic stress disorder (PTSD), stress and anxiety. According to an exemplary embodiment the disease is PTSD. In one embodiment, said subject is a mammal, preferably a human.

According to another aspect, there is provided a peptide (e.g., SEQ ID NO: 1) of the invention or a pharmaceutical composition comprising same for use in treating, preventing or alleviating a disease in a subject, particularly a disease associated with fear-related memory formation.

According to another aspect, there is provided use of a peptide of the invention (e.g., SEQ ID NO: 1) or a pharmaceutical composition comprising same for the preparation of a medicament for treating, preventing or alleviating a disease in a subject, particularly a disease associated with fear-related memory formation.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE FIGURES

Non-limiting examples of embodiments of the invention are described below with reference to figures attached hereto that are listed following this paragraph.

Figure 3:
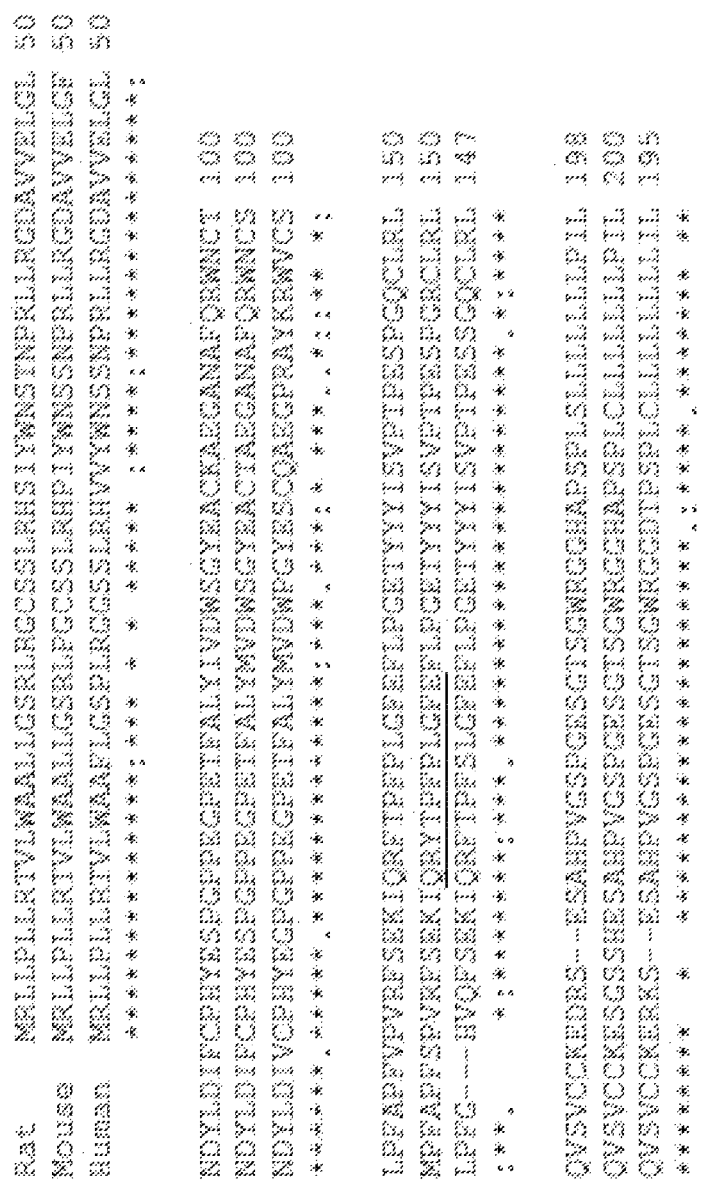

FIG. 3 shows the sequence of Eprhin A4 of rat, mouse and human with the G-H loop underlined.

DETAILED DESCRIPTION OF THE INVENTION

Figure 1A:
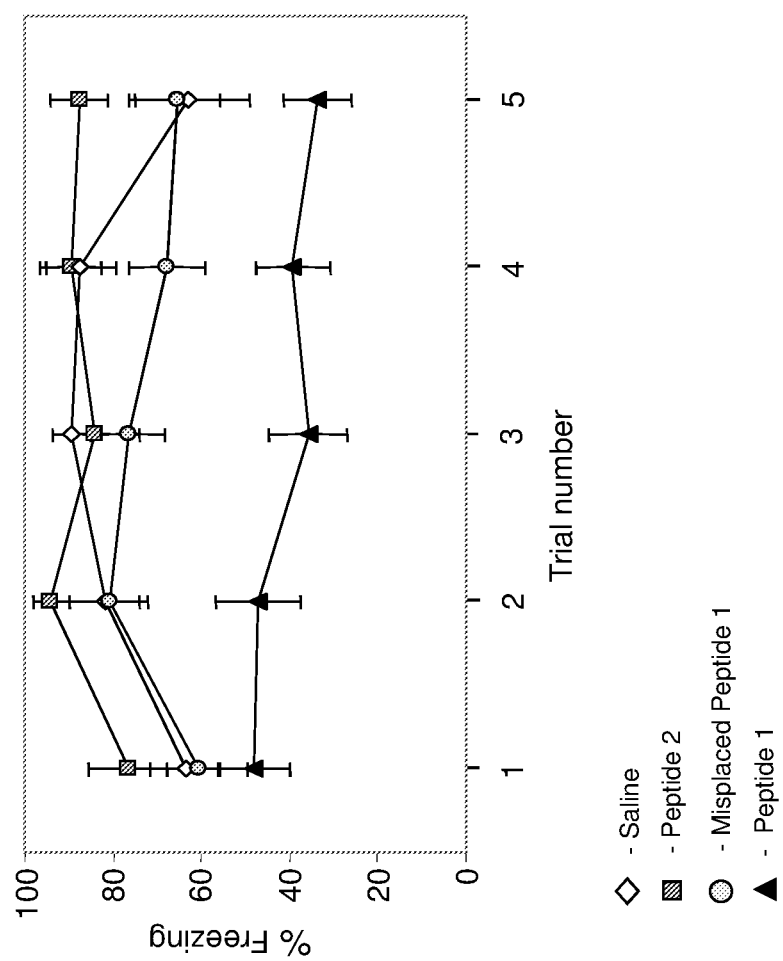
FIG. 1A shows a graph showing effect of test peptides and saline on long term-memory in rats as determined by percentage of freezing in rats in a fear conditioning model, indicating the ability of peptide 1 injected into the lateral and basal amygdala to inhibit freezing in rats relative to control peptide 2 that do not bind EphA, saline and misplaced peptide 1, which was injected to areas outside of the lateral and basal amygdale.

The present invention provides in some embodiment EphAs receptor inhibitor peptides, and particularly EphA4 receptor inhibitor peptides. In some embodiments, the peptides comprise a sequence derived from the G-H loop of ephrin A4. The invention further provides pharmaceutical compositions comprising said peptides and use thereof in treating, ameliorating or preventing diseases associated with memory formation.

As exemplified herein below, peptides (e.g., SEQ ID NO: 1) comprising a sequence of the G-H loop of ephrin A4 have specific binding affinity to EphA receptor, in particular the EphA4 receptor. Said binding was shown to also result in reduced ephrinA4-induced EphA4 tyrosine phosphorylation (FIG. 4C). Furthermore, an exemplary peptide was demonstrated as capable of inhibiting memory formation, in vivo, thereby indicating use of the peptides in treating diseases associated with memory formation in humans, including but not limited to post-traumatic stress disorder (PTSD).

According to some embodiments, the invention provides an isolated peptide comprising an amino acid sequence as set forth in SEQ ID NO: 1 (QRX$_1$TPFX$_2$LGFE), wherein X$_1$ is Tyr (Y) or Phe (F) and X$_2$ is Pro (P) or Ser (S), or a sequence having a conservative substitution relative to SEQ ID NO: 1. According to one embodiment, the peptide comprises the amino acid sequence selected from the group consisting of:

| | |
|---|---|
| (QRYTPFPLGFE); | SEQ ID NO: 2 |
| (QRFTPFSLGFE); | SEQ ID NO: 3 |
| (RRQRYTPFPLGFE); | SEQ ID NO: 4 |
| (RRQRFTPFSLGFE); | SEQ ID NO: 5 |
| (QRYTPFPLGFEK); | SEQ ID NO: 6 |
| (QRFTPFSLGFEK); | SEQ ID NO: 7 |
| (RRQRYTPFPLGFEK); and | SEQ ID NO: 8 |
| (RRQRFTPFSLGFEK); | SEQ ID NO: 9 |

According to some embodiments of the invention, the peptides may be between about 10 and 15 amino acids in length. The peptides may comprise a sequence having between about 8 and about 12 amino acids of the G-H loop of a mammalian (e,g., human, mouse or rat) ephrin A4. In some embodiments, the peptide comprises at least 8, at least 9, at least 10, at least 11 amino acids derived from, or corresponds to, the G-H loop of a mammalian ephrin A4.

The additional amino acids may be sequences derived from ephrin A4, or may be sequences that are derived from other sources. As exemplified herein below, the peptide retains its inhibitory function when comprising additional arginine residues contiguous to the peptide's N-terminus. Accordingly, in some embodiments, the peptide is selected from SEQ ID NO: 4 (RRQRYTPFPLGFE), SEQ ID NO: 5 (RRQRFTPFSLGFE); SEQ ID NO: 8 (RRQRYTPFPLGFEK); or SEQ ID NO: 9 (RRQRFTPFSLGFEK). According to an additional embodiment, the N-terminus of said peptide is acetylated. With respect to this embodiment, the peptide may have a length of no more than 20 amino acids, no more than 19 amino acids, no more than 18 amino acids, no more than 17 amino acids, no more than 16 amino acids, no more than 15 amino acids, no more than 14 amino acids, no more than 13 amino acids or no more than 12 amino acids.

According to another embodiment, the peptide further comprises at least one lysine residue contiguous to the peptide's C-terminus. In yet another embodiment, said peptide is biotinylated via said lysine residue.

According to an embodiment of the invention, the EphA receptor inhibitor peptides comprise a sequence derived from the G-H loop of ephrin A4. It will be apparent to those skilled in the art that human ephrin A4 may have various isoforms or variants, including but not limited to those of GenBank accession no. CAA06993.1; CAA06992.1;

AAI07484.1; NP_872631.1; NP_005218.1; NP_872632.2; EAW53140.1; EAW53139.1; or EAW53138.1. In some embodiments, the ephrin A4 may be from another source such as murine (Accession no. NP_031936.2; EDL15210.1; O08542.2; AAI07484.1; AAI60329.1; NP_872631.1; NP_005218.1; NP_872632.2; BAE25127.1; BAB28092.1; AAB50238.1; XP_006976391.1; or XP_006976390.1). As used herein, the human G-H loop of ephrin A4 corresponds to the amino acid sequence QRFTPFSLGFE (SEQ ID NO: 3) of ephrin A4 and the murine G-H loop of ephrin A4 corresponds to the amino acid sequence QRYTPFPLGFE (SEQ ID NO: 2) of ephrin A4.

In one embodiment, the peptide is other than the amino acid sequence as set forth in SEQ ID NO: 11 (RFTPFSLG-FEFLP).

The term "peptide" as used herein encompasses native peptides (degradation products, synthetic peptides or recombinant peptides), peptidomimetics (typically including non peptide bonds or other synthetic modifications) and the peptide analogues peptoids and semipeptoids, and may have, for example, modifications rendering the peptides more stable while in the body or more capable of penetrating into cells.

The terms "polypeptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to aspartic acid (D). According to an embodiment of the invention, the peptide of the invention comprises a sequence derived from the G-H loop of ephrin A4, with a conservative substitution. A conservative substitution is recognized in the art as a substitution of one amino acid for another amino acid that has a similar property. Exemplary conservative substitutions are set out in the Table 1 below:

| Amino Acid Property | Conservatively Substitutable Amino Acids |
| --- | --- |
| Non-polar | G A P I L V |
| Polar-uncharged | C S T M N Q |
| Polar-charged | D E K R |
| Aromatic | H F W Y |
| Other | N Q D E |

According to an embodiment of the invention, the peptide (i.e., the EphA receptor inhibitor peptide) comprises a sequence homologous to a sequence of the G-H loop of ephrin A4. According to an embodiment of the invention, the peptide comprises a sequence having greater 75%, 80%, 85%, 90% or 95% homology to a sequence of the G-H loop of ephrin A4. According to another embodiment, the peptide comprises a sequence having greater 75%, 80%, 85%, 90% or 95% homology to a sequence of SEQ ID NO:1. Each possibility represents a separate embodiment of the present invention.

The phrase "conservative substitution" also includes the use of a chemically derivatized residue in place of a non-derivatized residue provided that such peptide displays the requisite function of binding to EphA4 receptor and or affecting (e.g., inhibiting) memory formation as specified herein.

Typically, the present invention encompasses derivatives of the peptides. The term "derivative" or "chemical derivative" includes any chemical derivative of the peptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-NH2 acylation, acetylation, or thioglycolic acid amidation, and by terminal-carboxylamidation, e.g., with ammonia, methylamine, and the like. Peptides can be either linear, cyclic or branched and the like, which conformations can be achieved using methods well known in the art.

The peptide derivatives and analogs according to the principles of the present invention can also include side chain bond modifications, including but not limited to —CH2-NH—, —CH2-S—, —CH2-S=0, OC—NH—, —CH2-O—, —CH2-CH2-, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C-0-0-C (R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (Me Ala), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide analogs, which can contain one or more D-isomer forms of the amino acids. Production of retro-inverso D-amino acid peptides where at least one amino acid, and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide is capable of displaying the requisite function of binding to EphA4 receptor and or affecting (e.g., inhibiting) memory formation as specified herein.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

The peptides of the invention may be synthesized or prepared by techniques well known in the art. The peptides can be synthesized by a solid phase peptide synthesis method of Merrifield (see J. Am. Chem. Soc, 85:2149, 1964). Alternatively, the peptides of the present invention can be synthesized using standard solution methods well known in the art (see, for example, Bodanszky, M., Principles of Peptide Synthesis, Springer-Verlag, 1984) or by any other method known in the art for peptide synthesis.

In general, these methods comprise sequential addition of one or more amino acids or suitably protected amino acids to a growing peptide chain bound to a suitable resin.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5 dimethoxybenzyloxycarbonyl, o-nitrophenylsulfenyl, 2-cyano-t-butyloxycarbonyl, 9-fluorenylmethyloxycarbonyl (FMOC) and the like.

In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

The peptides of the invention may alternatively be synthesized such that one or more of the bonds, which link the amino acid residues of the peptides are non-peptide bonds. These alternative non-peptide bonds include, but are not limited to, imino, ester, hydrazide, semicarbazide, and azo bonds, which can be formed by reactions well known to skilled in the art.

The peptides of the present invention, analogs or derivatives thereof produced by recombinant techniques can be purified so that the peptides will be substantially pure when administered to a subject. The term "substantially pure" refers to a compound, e.g., a peptide, which has been separated from components, which naturally accompany it. Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

Included within the scope of the invention are peptide conjugates comprising the peptides of the present invention derivatives or analogs thereof joined at their amino or carboxy-terminus or at one of the side chains via a peptide bond to an amino acid sequence of a different protein. Conjugates comprising peptides of the invention and a protein can be made by protein synthesis, e. g., by use of a peptide synthesizer, or by ligating the appropriate nucleic acid sequences encoding the desired amino acid sequences to each other by methods known in the art, in the proper coding frame, and expressing the conjugate by methods commonly known in the art. Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

According to an embodiment of the invention, the EphA receptor inhibitor peptide is conjugated to an agent which modulates the peptide's biological activity. According to an embodiment of the invention, the agent which modulates the peptide's biological activity is an agent designed to increase the half-life of the peptide in the bloodstream, for example polyethylene glycol. According to an embodiment of the invention, the agent which modulates the peptide's biological activity enhances penetration of the blood-brain barrier by the peptide, for example, an agent having a lipophilic moiety.

According to an embodiment of the invention, the EphA receptor inhibitor peptide is conjugated to an agent which allows for the binding or detection of the peptide. According to an embodiment of the invention, the agent which allows for the binding or detection of the peptide is biotin.

According to an embodiment of the invention, the peptide of the invention has increased selectively to EphA receptor, particularly to EphA4 receptor. In some embodiments, the peptide of the invention has substantially greater selectively to EphA4 receptor as compared to other Eph receptors. As used herein, the term "selectively" is meant having a binding affinity for one or a few Eph receptor family members that is substantially greater than said binding affinity for the other known Eph receptor family members. As used in connection with selective binding affinity, "substantially greater" means at least a two-fold, at least a three-fold, at least a four-fold, at least a five-fold, at least a six fold, at least a seven-fold, at least a eight-fold, at least a nine-fold, at least a ten-fold, at least a fifteen-fold, at least a twenty-fold, at least a thirty-fold, at least a forty-fold, at least a fifty-fold or at least a hundred-fold increase in the amount of peptide bound to a receptor.

Pharmaceutical Compositions of the Invention

In some embodiments, there is provided pharmaceutical compositions comprising as an active ingredient a therapeutically effective amount of a peptide of the present invention (e.g., SEQ ID NO: 1), and a pharmaceutically acceptable carrier.

The pharmaceutical compositions of the invention can be formulated in the form of a pharmaceutically acceptable salt of the peptides of the present invention or their analogs, or derivatives thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The compositions can take the form of solutions, suspensions, emulsions, tablets, pills, capsules, powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of the peptide of the invention, preferably in a substantially purified form, together with a suitable amount of carrier so as to provide the form for proper administration to the subject.

An embodiment of the invention relates to a peptide presented in unit dosage form and are prepared by any of the methods well known in the art of pharmacy. In an embodiment of the invention, the unit dosage form is in the form of a tablet, capsule, lozenge, wafer, patch, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

Depending on the location of the tissue of interest, the peptides of the present invention can be supplied in any manner suitable for the provision of the peptide to cells within the tissue of interest. Thus, for example, a composition containing the peptides of the present invention can be introduced, for example, into the systemic circulation, which will distribute said peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

In an embodiment of the invention, peptides are administered via oral, rectal, vaginal, topical, nasal, ophthalmic, transdermal, subcutaneous, intramuscular, intraperitoneal or intravenous routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

For topical application, a peptide of the present invention, derivative, analog or a fragment thereof can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

The compositions of the present invention are generally administered in the form of a pharmaceutical composition comprising at least one of the active components of this invention together with a pharmaceutically acceptable carrier or diluent. Thus, the compositions of this invention can be administered either individually or together in any conventional oral, parenteral or transdermal dosage form.

Pharmaceutical compositions according to embodiments of the invention may contain 0.1%-95% of the active components(s) of this invention, preferably 1%-70%. In any event, the composition or formulation to be administered may contain a quantity of active components according to embodiments of the invention in an amount effective to treat the condition or disease of the subject being treated.

In an embodiment of the invention, the daily dosage of the peptide is between 0.1 mg and 1500 mg.

The peptides of the present invention, derivatives, or analogs thereof can be delivered in a controlled release system. Thus, an infusion pump can be used to administer the peptide such as the one that is used, for example, for delivering insulin or chemotherapy to specific organs or tumors. In one embodiment, the peptide of the invention is administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

Use of the Peptides

In the examples described below, results of animal experiments that were carried out to determine effects of an inhibitor of the EphA receptor comprising a sequence derived from the G-H loop of ephrin A4 are provided and described. Implications of the experimental results for the use and administration of an inhibitor of the EphA receptor comprising a sequence derived from the G-H loop of ephrin A4, and in particular, peptide 1 in humans in accordance with embodiments of the invention are discussed.

The experiment results indicate that the peptides of the invention are EphA4 antagonists. As used herein, "antagonist" refers to a biologically active ligand which binds to its complementary biologically active receptor and inhibits the physiological response of the receptor.

In some embodiment of the invention, the peptides and composition of the invention are useful for treating or ameliorating affective disorders, particularly anxiety disorders. "Affective disorders" or "mood disorders" as used herein, relate to a set of psychiatric diseases, including depression, bipolar disorder, and anxiety disorder.

Anxiety disorders are characterized by feelings of nervousness, anxiety, and even fear. They are several types of anxiety disorders, including: social anxiety (i.e., anxiety caused by social situations); post-traumatic stress disorder (PTSD, i.e., anxiety, fear, and flashbacks caused by a traumatic event); generalized anxiety disorder (i.e., anxiousness and fear in general, with no particular cause); panic disorder (i.e., anxiety that causes panic attacks); and obsessive-compulsive disorder (i.e., obsessive thoughts that cause anxiety and compulsive actions.

Depression, or major depressive disorder, is characterized by feelings of extreme sadness and hopelessness, with experience episodes that last for several days or even weeks. A milder form of depression is called dysthymia. Bipolar disorder means having periods of depression, and periods of mania, i.e., periods of the subject feeling extremely positive and active, resulting in irritable, aggressive, impulsive, and even delusional behavior.

Non limiting examples of affective disorders include, but are not limited to anxiety disorders (e.g., generalized anxiety disorder (GAD), social anxiety disorder (SAD; alternatively known as social phobia), panic disorder (with or without agoraphobia), posttraumatic stress disorder (PTSD), obsessive-compulsive disorder (OCD), separation anxiety disorder), mood disorders (e.g., depressive disorder, bipolar disorder) and psychotic disorders (e.g., schizophrenia, schizoaffective disorder, delusional disorder), substance-related disorders (e.g., substance abuse, substance-induced disorder, substance withdrawal).

In some embodiments, the present invention provides methods of treating a psychiatric condition selected from a neuropsychiatric disorder, an affective disorder, depression, hypomania, panic attacks, anxiety, excessive elation, bipolar depression, bipolar disorder (manic-depression), seasonal mood (or affective) disorder, schizophrenia and other psychoses, anxiety syndromes, anxiety disorders, phobias, stress and related syndromes, cognitive function disorders, aggression, drug and alcohol abuse, obsessive compulsive behavior syndromes, borderline personality disorder, non-senile dementia, post-pain depression, post-partum depression, cerebral palsy, post-traumatic stress disorder (PTSD), and combinations thereof.

The present invention provides a method of treating disorders characterized by aversive, unwanted, disturbing, traumatic, fearful, intrusive, repetitive or stereotyped memories, thoughts, perceptions or behaviors, comprising administering to a patient in need thereof a therapeutically effective amount of a peptide or composition of the invention. Furthermore the invention relates to the use of said peptides for such a treatment, and to the use of said peptides for the manufacture of a medicament for the treatment of the mentioned disorders. Such disorders include, but are not limited to, phobias, posttraumatic stress disorder and obsessive-compulsive disorder.

Phobias are characterized by marked and persistent fear that is excessive or un-reasonable, cued by the presence or anticipation of a specific object or situation (e.g., flying, heights, animals, receiving an injection, seeing blood, social, performance). Exposure to the phobic stimulus almost invariably provokes retrieval of stimulus-associated fearful memories, which results in an immediate anxiety response. The avoidance, anxious anticipation, or distress in the feared situation(s) interferes significantly with the person's normal routine, occupational functioning, or social activities or relationships, or there is marked distress about having the phobia. The defining criteria for a diagnosis of phobias can be found in the Diagnostic and Statistical Manual of Mental Disorders-Fourth Edition (DSM-IV), published by the American Psychiatric Association, Washington D.C., 1994. Psychological treatment options of phobias include desensitization and exposure (for specific phobias) and cognitive behavioral therapy (for social phobias). Pharmacological treatment options include beta-blockers, selective serotonin reuptake inhibitors and monoamine oxidase inhibitors. The effects of psychological treatment (exposure, cognitive restructuring, social skills training) and pharmacological treatments (selective serotonin reuptake inhibitors, monoamine oxidase inhibitors) for social phobia result in a reduction in anxiety and, in most cases, a weakening of the tendency to avoid, but the effects are not of such a magnitude as to result in remission.

Obsessive-Compulsive Disorder (OCD) is an anxiety disorder characterized by recurrent obsessions or compulsions sufficient to cause marked distress. These behaviors are time-consuming, or significantly interfere with the person's normal functioning, social activities or relationships. Obsessions are recurrent ideas, thoughts, images, or impulses that enter the mind and are persistent, intrusive, and unwelcome. Compulsions are repetitive, purposeful behaviors performed in response to an obsession, and are designed to neutralize or prevent discomfort or some dreaded event or situation. However, the activity is excessive, or not connected realistically with that which it is designed to prevent. The defining criteria for a diagnosis of OCD are well known to a skilled artisan. Psychological treatment options of OCD include cognitive-behavioral techniques. Pharmacological treatment options include serotonin reuptake inhibitors. However, not all patients with OCD respond to serotonin reuptake inhibitors, some do not tolerate them, and many have only a partial response.

Post-traumatic stress disorder (PTSD) is a debilitating psychiatric disorder induced by exposure to a severe trauma and is typically associated with functional impairments and increased physical and mental health risks. PTSD patients tend to have a six fold higher risk of suicide than non-PTSD patients. The treatment of PTSD is challenging, and may include many years of individual and group therapy and treatment with medications such as antidepressants, anxiolytic drugs, β-adrenergic antagonists, opiates, or cortisol with variable results.

The experiment results indicate that treatment protocols in accordance with embodiments of the invention can be advantageous in preventing and treating post-traumatic stress disorder (PTSD).

Peptides according to embodiments of the invention may be administered to patients showing symptoms of PTSD. In addition, peptides according to embodiments of the invention may be administered to a patient who has undergone a traumatic event. In an embodiment, the traumatic event is abuse, domestic violence, violent crime, rape, fire, natural disaster, combat, vehicular accident, medical emergency, death of friend or relative and terror. None limiting examples of subjects who may be treated according to the principles of the present invention include a combat soldier, a firefighter, a law-enforcement officer, a police officer, a medical practitioner or an emergency medical responder.

In an embodiment, a subject at risk of PTSD is a subject who has scored an above average score on a trauma history questionnaire.

In an embodiment of the invention, peptides according to embodiments of the invention are administered to a subject who is at risk of experiencing a traumatic event. Accordingly, peptides may be administered any time before or after experiencing a traumatic event or before or after reconsolidation treatment.

According to an embodiment of the invention, peptides according to embodiments of the invention are administered after a subject experiences a traumatic event. In an embodiment, peptides according to embodiments of the invention are administered up to 24 hours (e.g., between 1 minute and 1 day) following the traumatic event. In an embodiment, peptides according to embodiments of the invention are administered between 24 hours and one week following the traumatic event. In an embodiment, peptides according to embodiments of the invention are administered between 1 week and 1 month following the traumatic event.

According to an embodiment of the invention, a subject who has experienced a traumatic event may recall and actively consolidate memory of a traumatic event in a process called "reconsolidation," and may be simultaneously treated with a peptide according to an embodiment of the invention. The subject may be treated with a peptide according to an embodiment of the invention up to 24 hours prior to reconsolidation. The subject may be treated with a peptide according to an embodiment of the invention between 1 minute and 6 hours or between 6 and 24 hours subsequent to reconsolidation.

A "therapeutically effective amount" of the peptide is that amount of peptide which is sufficient to provide a beneficial effect to the subject to which the peptide is administered. More specifically, a therapeutically effective amount means an amount of the peptide effective to prevent, alleviate or ameliorate tissue damage or symptoms of a disease of the subject being treated.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Example 1

Manufacture of Peptides

A peptide derived from the G-H loop of ephrinA4 having the sequence Ac-RRQRYTPFPLGFE-Lys(Biotin)-NH2-0H (SEQ ID NO: 8), hereinafter referred to as peptide 1, was manufactured by GL Biochem (Shanghai) Ltd (http://www.glbiochem.com) using solid-phase synthesis. As a control peptide, a peptide derived from an E helix site of ephrinA4 having the sequence Ac-RRWSGYEACTAEG-Lys(Biotin)-NH2-0H (SEQ ID NO: 10), hereinafter referred to as peptide 2, was manufactured by the same manufacturer using similar procedures. Both peptides were biotinylated via a lysine side chain for detection in models. Purity of both peptides was determined to be greater than 95% using high-performance liquid chromatography using ultraviolet detection at 214 nanometers.

Example 2

In Vitro Pull Down Model Using Rat Brain Homogenate

A pull-down assay was performed to test the affinity of peptide 1 and peptide 2 to EphA4 receptor. Homogenized rat brain was used as a source for EphA4 receptor. Rat brains were homogenized with Tris(tris(hydroxymethyl)aminomethane) buffer comprising 50 millimolar (mM) tris, 1% NP-40 and 2 mM ethylenediaminetetraacetic acid. Peptides 1 and 2, in amounts of 20 micrograms, were respectively incubated for 1 hour with equal amounts of brain lysate diluted with 50 mM Tris buffer at room temperature, followed by incubation for 1 hour with 50 microliters of Streptavidin Agarose. The samples were washed with 50 mM Tris buffer. Proteins were then eluted with boiled sample buffer and separated using gel electrophoresis (SDS-PAGE).

Western blot analysis was then performed to determine binding affinity to EphA4 receptor. Blots were blocked with blocking buffer (5% non-fat dry milk in wash buffer (10 mM Tris pH 7.5, 100 mM NaCl, 0.1% Tween 20)) for 1 hour at room temperature. Blots were then subjected to purified mouse anti-EphA4/Sek monoclonal antibodies, (1:3000—BD Transduction Laboratories) or rabbit eEF2 (elongation factor 2) antibody (1:1000—Cell Signaling) in blocking buffer for 1 hour at room temperature. The blots were then subjected to horseradish peroxidase-conjugated anti-mouse or anti-rabbit IgG (1:1500—Jackson ImmunoResearch Laboratories) in wash buffer for 1 hr at room temperature. Blots were washed with wash buffer for 30 minutes. The blots were subjected to electrochemiluminescence for 1 minute and visualized and quantified using a charge-coupled device camera (XRS; Bio-Rad).

Figure 2:
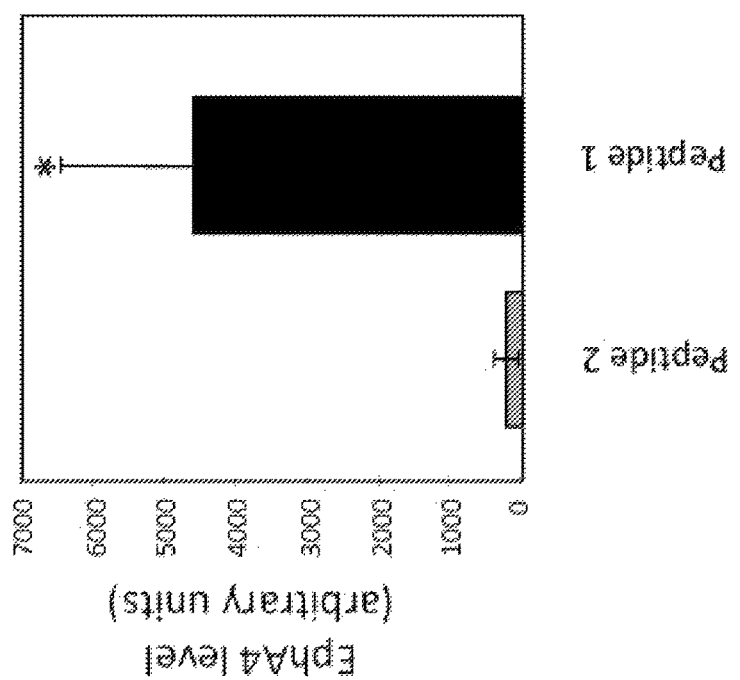
FIG. 2 shows a histogram showing strong binding affinity of peptide 1 to EphA4 receptor relative to peptide 2 based on an in vitro pull down model using rat brain homogenate.

The experiment showed that peptide 1 binds the EphA4 receptor whereas Peptide 2 does not, as is evident in FIG. 2. Peptide 1 did not bind the eukaryotic elongation factor 2 (eEF2) which served as a control, indicating that Peptide 1 is specific in its interaction with EphA4 receptor, and may potentially be used as a specific agent to bind EphA receptor, in particular, EphA4 receptor.

Example 3A

Fear Conditioning In Vivo Model

Fear conditioning is a procedure in which groups of animals are trained to associate a neutral stimulus, such as a tone, with an aversive event. Subsequently, the neutral stimulus is administered to the groups of animals, and the animals' responses are analyzed. A test group of animals is administered a test agent which may inhibit the long term association in the memory of the animals between the neutral stimulus and the aversive event. If at a point in time about 24 hours after training the animals in the test group respond to the stimulus to a lesser degree than the animals in the control group without having other significant side effects, the test agent is determined to inhibit formation of long term memories. Such an agent may be considered for use in treatment of a disease associated with memory formation, for example PTSD. It is most desirable for an agent used in PTSD to inhibit long term memory formation, but not to inhibit short term memory formation. Short term memory formation was also tested in the current model by testing responses to stimulus 60 minutes after training.

In the current model, neutral stimulus provided to the animals was a tone and the aversive event was a mild footshock provided to the animals.

Long-term memory formation is believed to involve modifications in neural transmission and/or synaptic connections in neural networks in the area of the brain known as the lateral amygdala (LA.) In the current model, Peptide 1 was used a test agent and was administered directly to the LA.

In the model, male Sprague Dawley rats (each weighing about 250-300 grams), were used in the study (animals were obtained from Harlan Laboratories). In order to administer test agents to the LA of the rats, surgery was performed in which cannulas were inserted. To perform the surgery, rats were anesthetized with Xylazine 2% (15 milligrams per kilogram [mg/kg]) and Ketamine (120 mg/kg). Calmagine (Vetoquinol) (0.01 milliliters) was injected for analgesia before surgery. Guide stainless-steel cannulas (23 gauge) were implanted bilaterally 1.5 millimeters (mm) above the LA. The animals recovered for 5-7 days before behavior training.

Following surgery, rats were housed separately at 22±2° C. in a 12 hour light/dark cycle, with free access to food and water. Behavioral experiments were approved by the University of Haifa Institutional Committee for animal experiments in accordance with National Institutes of Health guidelines.

Rats were habituated to the training chamber and to the injection machine for 2 days for 30 min each day. On the next day the animals were subjected to the fear conditioning protocol. Animals were randomized into three groups: saline control group (6 animals), to which saline was administered; peptide 1 group (9 animals), to which peptide 1 was administered, and peptide 2 group (6 animals) to which peptide 2, a control peptide which does not inhibit EphA4 receptor, was administered. The stylus was removed from the guide cannula and a 28 gauge injection cannula, extending 1.5 mm from the tip of the guide cannula aimed to the LA was carefully placed.

The injection cannula was connected via polyethylene (PE20) tubing, back filled with saline with a small air bubble separating the saline from the peptide solution, to a 10 μl Hamilton micro-syringe, driven by a microinjection pump (CMA/100, Carnegie Medicine; or PHD 2000, Harvard Apparatus). Solution was injected at a rate of 0.5 microliter per minute (μl/min). Total volume injected per amygdala was 0.5 μl. Peptide 1 and Peptide 2 were each dissolved in saline at concentration of 10 μg/μl. Following injection, the injection cannula was left for an additional 1 min before withdrawal to minimize dragging of injected liquid along the injection track.

30 minutes after administration of either saline or either of the peptides, animals were introduced into the training chamber. 300 seconds after introduction into chamber animals were presented with five pairings of tone (Conditioned stimulus [CS] for a length of 40 seconds, at a frequency of 5 kilohertz and an intensity of 80 decibel) that co-terminated with a foot shock (Unconditioned stimulus [US] which lasted for 0.5 sec, at a current of 1.5 milliampere). The interval between tones was random with an average of 180 seconds.

Rat groups were then tested in a different cage, 1 hour after training for short-term memory or 24 hours after training for long-term memory. Three hundred seconds after the start of the testing animals were subjected to 5 tone presentations (40 sec, 5 kHz, 80 dB) with an average inter trial interval of 180 seconds.

Freezing was calculated by a video camera placed in the chamber which analyzed movement of animals upon tone presentations. The results were summed and averaged for each group and were expressed in terms of percentage of time of tone presentations that animals were frozen.

After behavioral analysis was completed, rats were sacrificed and brains were quickly removed, placed on dry ice and stored at −80° C. until use. Brains were sliced (50 μm) and stained with cresyl violet acetate to verify cannula placements. Only rats with cannula tips at or within the boundaries of the lateral and basal amygdala (LBA) were included in the data analysis.

The results of the analysis of freezing 24 hours after training are shown in a graph in FIG. 1A. The results indicate that rats microinjected with peptide 1 froze significantly less ($p<0.004$) than animals injected with saline ($p<0.04$), peptide 2 ($p<0.005$) or animals injected with peptide 1 in areas adjacent to the LA ($p<0.03$), showing that peptide 1 animals are impaired in long term fear memory. Peptide 1 did not alter the rate of fear reduction over the trials when compared to controls. These results indicate that ephrinA4 interaction in LA occurs in long-term fear conditioning memory, and peptide 1 is able to block long-term fear conditioning memory.

The results of freezing analysis 1 hour after training indicate no main effect for groups ($p>0.4$). These results show that ephrinA4 is not involved in formation of short term memory and peptide 1 does not inhibit formation of short term memory.

In addition, freezing before the training (pre-CS) or postshock during training was not affected by the treatment, indicating that peptide 1 does not affect freezing per se, foot shock sensitivity and US processing in the LA. Cumulatively, the aforementioned findings demonstrate that the peptide 1 in LA has no effect on faculties needed for CS-US association but rather on their consolidation into long term memory.

Example 3B

Fear Conditioning In Vivo Model, Systemic Administration

Figure 1B:
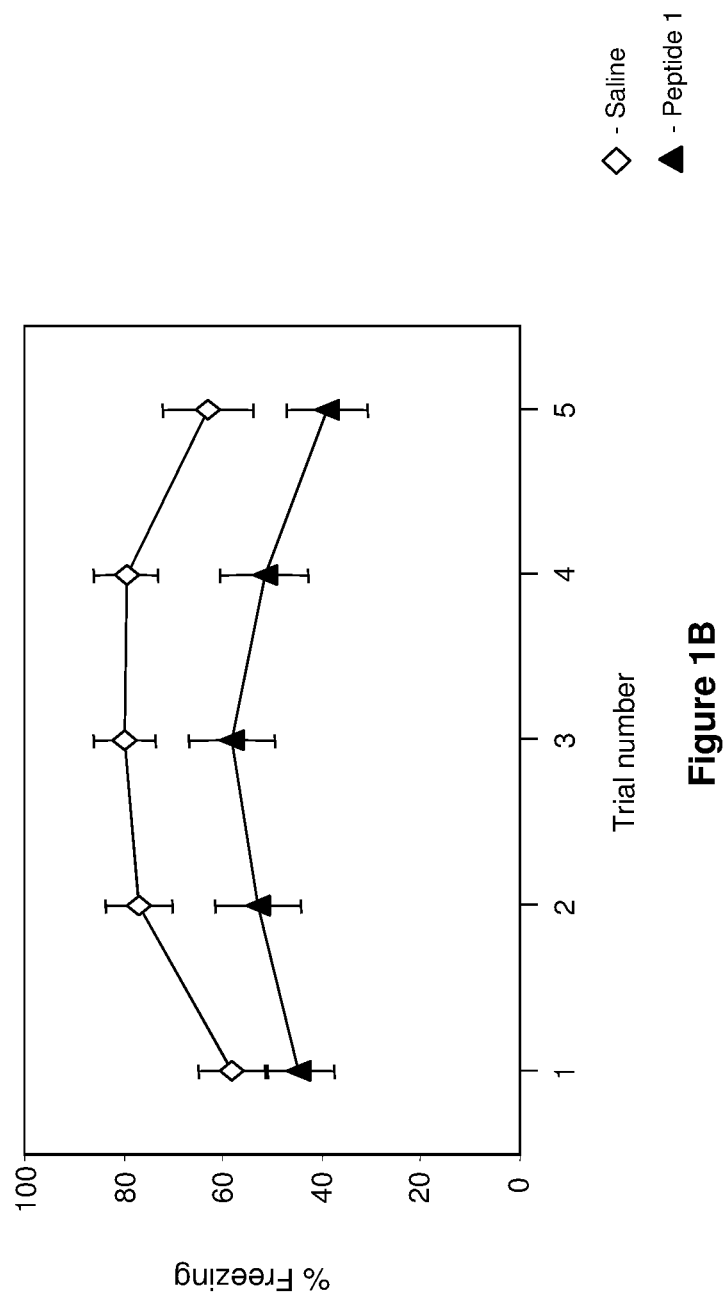
FIG. 1B shows a graph showing effect of peptide 1 on inhibition of freezing in rats relative to saline, in a Fear Conditioning Model; when both agents were administered systemically.

A fear conditioning in vivo model was performed as in example 3A, however, no cannula was introduced into the rats. The rats were administered either saline (n=14) or peptide 1 (n=15) through a subcutaneous injection, 1 hour after fear conditioning. The rats were administered a single dose of 20 μl of a composition having a concentration of 10 μg/μl of peptide 1, or an equivalent amount of saline. A fear memory test was performed 24 hours after the injection. As shown in FIG. 1B, administration of Peptide 1 systemically, through the subcutaneous route, was effective in significantly reducing freezing relative to saline.

These results show that Peptide 1 is effective in block long-term fear conditioning memory, even when administered systemically. Peptide 1 may be a viable agent for treating disease associated with fear-related memory formation, even when administered systemically, for example, subcutaneously.

Example 4

Methods of Treating a Human Subject to Prevent and/or Treat PTSD

Figure 4A:
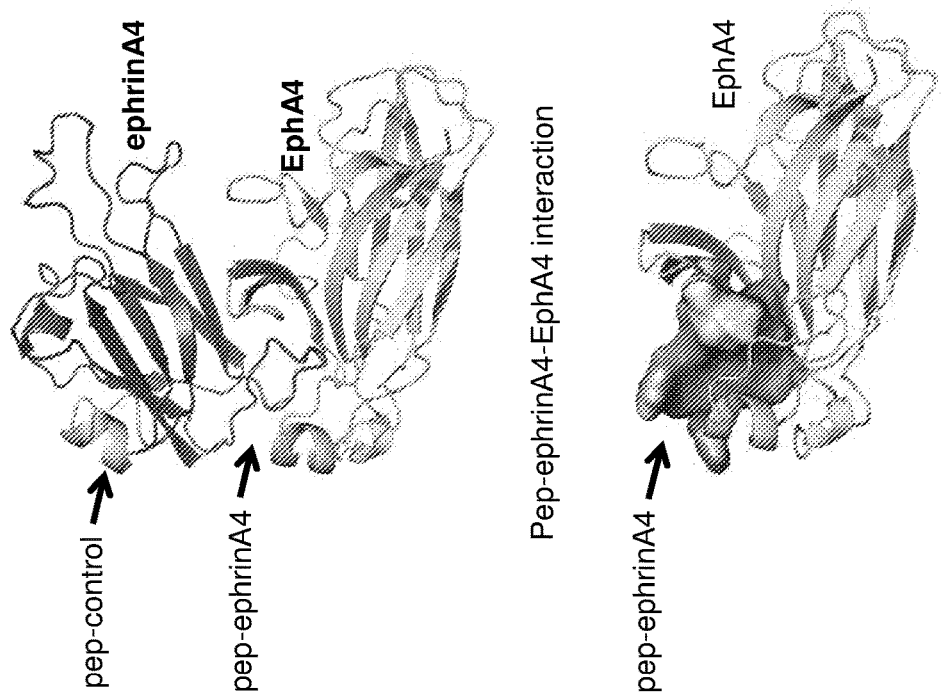
FIG. 4A shows a molecular model of ephrinA4 binding to EphA4 receptor using the Swiss-Model. Upper figure: The ephrinA4 peptide (pep-ephrinA4) is derived from the GH loop binding domain of ephrinA4. The control peptide (pep-control) is derived from E helix of the ephrinA4. Lower figure: A molecular model of pep-ephrinA4 peptide bound to EphA4.
Figure 4B:
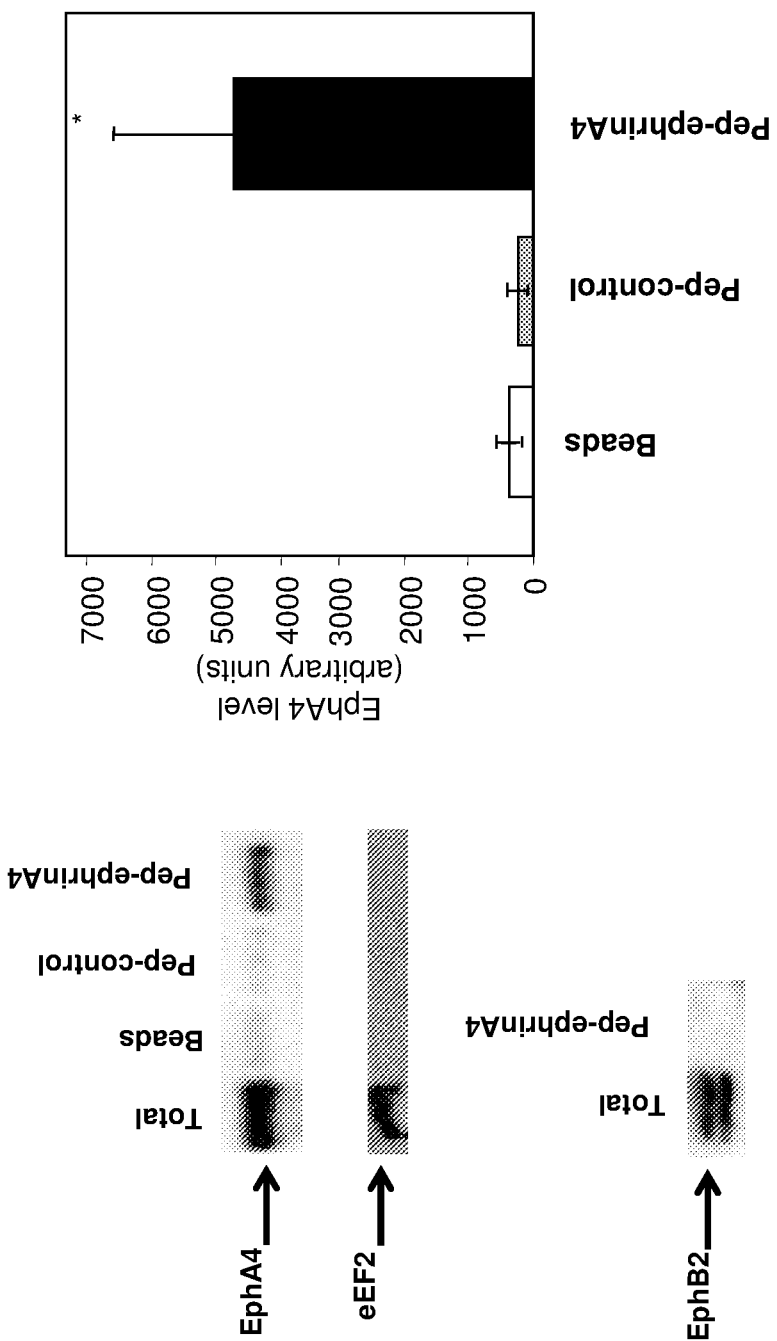
FIG. 4B shows Western blot analysis and a corresponding bar graph of a pull down assay, using the ephrinA4 peptide (pep-ephrinA4) compared to a control peptide (pep-control) or agarose beads alone.
Figure 4C:
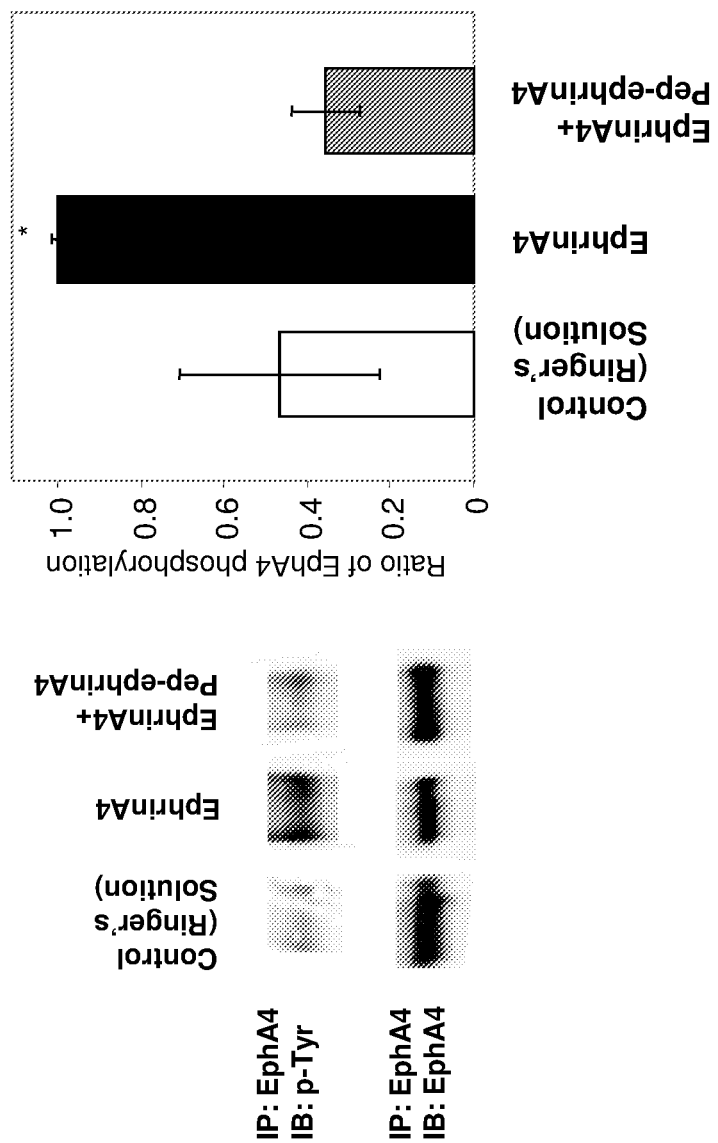
FIG. 4C shows the results of an immunoprecipitation assay and a corresponding bar graph of the ephrinA4 peptide and the ephrinA4 compared to ephrinA4 and Ringer's solution as controls.

FIG. 4A illustrates a molecular model of ephrinA4 binding to EphA4 receptor using the Swiss-Model. The upper panel shows that the ephrinA4 peptide (depicted "pep-ephrinA4") is derived from the GH loop binding domain of ephrinA4. The control peptide (pep-control) is derived from E helix of the ephrinA4. The lower panel shows a molecular model of pep-ephrinA4 peptide bound to EphA4.

A pull down experiment was performed indicating that pep-ephrinA4, but not pep-control or agarose beads alone, interacts with EphA4 (Figure B). The ANOVA analysis showed a significant effect for group ($F(2)=4.513$ $p<0.05$), and post hoc analysis found that more EphA4 was pulled down in the pep-ephrinA4 group (n=4) than in the pep-control ($p<0.04$; (n=3)) or beads ($p<0.03$; (n=4)). Pep-ephrinA4 did not interact with the EphB2 receptor or elongation factor 2 protein (eEF2) serving as control proteins.

These results show that ephrinA4 mimetic peptide interacts with EphA4 receptor and inhibits ephrinA4-induced EphA4 phosphorylation.

Further, brain slices that contain the amygdala were divide to 3 groups: 1) placed in Ringer's solution, 2) placed in Ringer's solution and stimulated with ephrinA4-Fc for 20 minutes or 3) placed in Ringer's solution with pep-ephrinA4 for 20 minutes followed by stimulation with ephrinA4-Fc for 20 minutes (n=3 each). Protein extracts from the slices were immunoprecipitated with anti-EphA4 antibody and subjected to Western blot with anti-EphA4 or anti-phosphotyrosine antibodies. The upper panel (FIG. 4C) shows that pep-ephrinA4 abolished ephrinA4-induced EphA4 receptor tyrosine phosphorylation. The lower panel shows the EphA4 protein level in immunoprecipitates. The ANOVA analysis showed a significant effect for group ($F(2)=5.496$, $p<0.05$), and post hoc analysis found significant increase in EphA4 phosphorylated in the ephrinA4 group when compared to the Ringer's solution control ($p<0.05$) or ephrinA4+pep-ephrinA4 ($p<0.03$) groups. The phosphorylation of EphA4 in the control Ringer's group is not significantly different from the ephrinA4+pep-ephrinA4 group ($p>0.6$). This indicates that Pep-ephrinA4 inhibits ephrinA4-induced EphA4 tyrosine phosphorylation.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. An isolated peptide, comprising the amino acid sequence as set forth in SEQ ID NO: 1 (QRX$_1$TPFX$_2$LGFE), wherein X$_1$ is Tyr (Y) and X$_2$ is Pro (P) or Ser (S), wherein said peptide is up to 14 amino acids long.

2. The peptide according to claim 1, comprising the amino acid sequence as set forth in SEQ ID NO: 2 (QRYTPFPLGFE).

3. The peptide according to claim 1, further comprising 1-4 arginine residues contiguous to the peptide's N-terminus, wherein said peptide is up to 14 amino acids long.

4. The peptide according to claim 3, comprising the amino acid sequence as set forth in SEQ ID NO: 4 (RRQRYTPFPLGFE).

5. The peptide according to claim 3, consisting of the amino acid sequence as set forth in SEQ ID NO: 4 (RRQRYTPFPLGFE).

6. The peptide according to claim 1, wherein the N-terminus of said peptide is acetylated.

7. The peptide according to claim 1, further comprising at least one Lysine residue contiguous to the peptide's C-terminus.

8. The peptide according to claim 7, comprising the amino acid sequence as set forth in SEQ ID NO: 6 (QRYTPFPLGFEK).

9. The peptide according to claim 1, wherein said peptide is an inhibitor of an ephrin type-A (EphA) receptor.

10. The peptide according to claim 9, wherein said EphA receptor is EphA4 receptor.

11. A pharmaceutical composition comprising as an active ingredient an isolated peptide according to claim 1, and a pharmaceutically acceptable carrier.

12. The pharmaceutical composition of claim 11, formulated for systemic administration.

13. The pharmaceutical composition of claim 12, wherein the systemic administration is selected from intravenous administration, subcutaneous administration, inhalation, intradermal administration, transdermal administration, transmucosal administration, and oral administration.

14. A method of inhibiting or reducing Ephrin A4-induced EphA4 receptor tyrosine phosphorylation or activation of EphA4 receptor by Ephrin A4 in a disease associated with fear-related memory formation mediated by Ephrin A4-induced EphA4 receptor tyrosine phosphorylation or by activation of EphA4 receptor by Ephrin A4, comprising administering to a patient in need thereof an effective amount of the peptide of claim 1.

* * * * *